United States Patent
Rogers (10) Patent No.: US 6,232,092 B1
(45) Date of Patent: May 15, 2001

(54) METHOD FOR PREPARING BIOLOGICAL SPECIMENS FOR VISUAL ANALYSIS

(75) Inventor: Rick A. Rogers, Needham, MA (US)

(73) Assignee: Rogers Imaging Corporation, Needham, MA (US)

( * ) Notice: Subject to any disclaimer, the term of this patent is extended or adjusted under 35 U.S.C. 154(b) by 0 days.

(21) Appl. No.: 09/165,820

(22) Filed: Oct. 2, 1998

(51) Int. Cl.$^7$ .................................................. G01N 1/30
(52) U.S. Cl. .................................................. 435/40.5
(58) Field of Search ........................................ 435/40.5

(56) References Cited

U.S. PATENT DOCUMENTS 5,344,637 * 9/1994 Camiener .................................. 424/3
6,017,725 * 1/2000 Hoffmann et al. .................. 435/40.5

OTHER PUBLICATIONS

Becker, David L. et al., "Enhancing The Laser Scanning Confocal Microscopic Visualization of Lucifer Yellow Filled Cells In Whole–Mounted Tissue" *Scanning Microscopy*, vol. 5, No. 3 pp. 619–624 (Sep. 1991).

Zill,Sasha N., et al., "Characterization of Insect Sense Organs And Optical Clearing Of Whole–Mount Preparations Using diI In Fixed Tissues", *J. exp. Biol.*, 175, pp. 299–303 (1993).

D.L. Gard, "Organization, Nucleation, and Acetylation of Microtubules in *Xenopus laevis* Oocytes: A Study by Confocal Immunofluorescence Microscopy," *Development Biology*, 143:346–362, (1991).

R.A. Rogers, et al., "3–D Confocal Microscopic Imaging of Amosite Fibers in Hamster Lungs," Sixth International Meeting on the Toxicology of Natural and Man–Made Fibrous and Non–Fibrous Particles, Sep. 15–18, (1996) (Abstract).

R.A. Rogers, et al., "Enhanced Contrast within Plastic Embedded Tissue by Lucifer Yellow CH—An Ideal Stain for Laser Scanning Confocal Microscopy," *Molecular Biology of the Cell*, 3(Suppl):185a(Sep. 1992).

R. Rogers, et al., "3–D Imaging of Respirable Size Asbestos Fibers in Rat and Human Lung Tissue," Proceedings Microscopy and Microanalysis 1995, p. 1018–1019, (Aug. 13–17, 1995).

M.W. Klymkowsky, "Whole–Mount Staining of Xenopus and Other Vertebrates," *Methods in Cell Biology*, 36:419–441 (1991).

R.P. Bolender, et al., "Lung Morphometry: A New Generation of Tools and Experiments for Organ, Tissue, cell, and Molecular Biology," *Am. J. Physiol.* 265 (*Lung Cell. Mol. Physiol. 9*) :L521–548, (1993).

J.P. Butler, et al., "Rheology and Spontaneous Oscillations in Xenopus Oocytes and Eggs," *FASEB J.*, 6(5): A1627, (1992).

J.A. Dent, et al., "A Whole–Mount Immunocytochemical Analysis of the Expression of the Intermediate Filament Protein Vimentin in Xenopus," *Development* 105:61–74, (1989).

M.S. Klempner, et al., "Invasion of Human Skin Fibroblasts by the Lyme Disease Spirochete, *Borrelia burgdoferi,*" *J. Infectious Diseases*, 167:1074–1081, (1993).

E. Oldmixon and R.A. Rogers, "Overcoming Confocal Scanning Laser Microscopy Depth Limitations," *FESEB J.*, 8:A691, (1994).

T.D. Sweeny et al., "Anesthesia Alters the Pattern of Aerosol Retention in Hamsters," *J. Appl. Physiol.*, 54:37–44 (1983).

K. Takahashi et al., "Cellular Markers that Distinguish the Phases of Hemangioma During Infancy and Childhood," *J. Clin. Invest.* 93:2357–2364, (1994).

E.R. Weibel, "Morphometric and Sterological Methods in Respiratory Physiology, Including Fixation Techniques," In: Otis, A.B. ed. Techniques in the Life Sciences P4/1, Elsevier, Ireland, p.1–35, (1984).

E. H. Oldmixon, "Functional Anatomy of the Alveolar Ductal Unit," Bioengineering Conference ASME, BED–vol. 24, pp. 147–150 (1993).

Klymkowsky M. Whole Mount Staining of Xenopus and Other Vertebrates. Methods in Cell Biology vol. 36, pp. 419–441, 1991.*

* cited by examiner

*Primary Examiner*—Ralph Gitomer
(74) *Attorney, Agent, or Firm*—Hamilton, Brook, Smith & Reynolds, P.C.

(57) ABSTRACT

The present invention provides a method to clarify and contrast stain intact biological tissue samples for microscopic analysis. Biological specimens are prepared for visual analysis by depigmenting specimen, staining the specimen non-specifically with fluorescent dye, and equilibrating the depigmented, non-specifically stained specimen in a clearing solution, wherein the refractive index of the clearing solution approximates that of the specimen. Visual analysis of the specimen can include, for example, determination of distribution, quantity and size of foreign material in the biological specimen. Also, the morphology of tissue surrounding foreign material can be assessed.

11 Claims, 7 Drawing Sheets

METHOD FOR PREPARING BIOLOGICAL SPECIMENS FOR VISUAL ANALYSIS

BACKGROUND OF THE INVENTION

The study of tissues for medical research, disease diagnosis, disease prognosis as well as the examination of tissues after in vivo or in vitro exposure to agents of interest requires the ability to examine the intact tissue in three dimensions at all depths. For example, it is useful to be able to examine an entire lobe of an animal's lung where the animal has been exposed to an inhaleable substance, such as insulation fiber, in order to determine the distribution, biopersistence and pulmonary toxicity of the substance in the lung tissue.

Whole mount imaging of organisms or tissues provides an immediate and three-dimensional view of the architecture and morphology of the organism or tissue. Current technology in confocal microscopy and deconvolution technology allow the visualization of different focal planes within a sample of interest. Using these techniques, a three dimensional reconstruction of a biological sample can be made. However, these technologies are limited to relatively thin sections of sample. Under normal imaging conditions, the depth of optical penetration into specimens is typically limited to 20–40 microns.

Three-dimensional information can also be gained by serial section analysis, but only following an indirect, time-consuming process. In addition, sectioning is subject to many preparation artifacts that can distort the morphology of the tissues under study and disrupt or distort the distribution of the agent of interest within the tissue.

The methods used to achieve controlled exposure of animals to substance of interest often introduce method specific artifacts, necessitating the use of more than one method of exposure in any given study. Current fiber imaging methodologies, such as ash analysis, limit important observations and interpretations to bulk fiber load and size class of fibers, and do not reveal fiber position or associations with relevant pulmonary structures, important to lung pathology. Furthermore, traditional methods, such as ash analysis, can destroy pertinent information, while other methods, such as serial sectioning can take a year or more to complete thorough analysis of a specimen.

For example, pulmonary toxicity of natural and man made fibers are assessed in animal models using two-exposure methods: aerosol and intratracheal instillation. While each has distinct advantages, under certain conditions, one method may be more appropriate than the other. When the precise dose of a material is required, intratracheal instillation may be the preferred method of administration. However, the possibility of uneven distribution induced by fiber agglomeration may cloud interpretation of results. Although many studies have addressed clearance of fibers in lungs, none have adequately addressed the problem of fiber agglomeration in airways resulting from the method of fiber administration to lungs.

SUMMARY OF THE INVENTION

The present invention relates to the preparation of biological tissue for microscopic evaluation of morphologic features such as tissue architecture. The present invention allows the visualization of morphologic features of cells and tissues within intact biological specimens at an unlimited depth of observation. The present invention enables examination and analysis of man made and/or naturally occurring foreign material contained within cells, tissues or organ structures without physical destruction or cutting of the specimen itself.

The present invention eliminates light scattering properties of opaque tissue surrounding the optical plane of focus of the imaging plane. Under normal imaging conditions, depth of optical penetration into specimens is limited to 20–40 microns. The method of the present invention allows a depth of penetration of at least 800 microns. Therefore, in the example of rat lung tissue, entire airways within a lobe can be directly observed without physical disturbance. The present invention allows the examination of entire airways anywhere within intact lung lobes. The present invention relates to a method for clarifying an intact biological specimen, wherein the biological specimen is rendered suitable for analysis. The method comprises the steps of staining the specimen, and equilibrating the stained specimen in a clearing solution having a refractive index approximately that of the specimen.

The present invention relates to a method of clarifying lung tissue, wherein the lung tissue is rendered suitable for analysis. The method comprises the steps of staining the lung tissue with Lucifer Yellow CH and equilibrating the lung tissue in a clearing solution, whereby the refractive index of the clearing solution approximates that of the lung tissue. The present invention reveals the position of foreign material and or association of such material with relevant, morphology in a biological tissue of interest.

The present invention allows the determination of distribution quantity and size of exogenously derived material present in an intact biological specimen. The method comprises the steps of staining the specimen, equilibrating the specimen in a clearing solution, whereby the refractive index of the clearing solution approximates that of the specimen and visualizing the exogenously derived particles.

The present invention allows the determination of distribution, quantity and size of exogenously derived fibers present in an intact lung specimen wherein the specimen is rendered suitable for analysis. The method comprises the steps of staining the lung specimen with Lucifer Yellow CH, equilibrating the lung specimen in a clearing solution, whereby the refractive index of the clearing solution approximates that of the lung specimen and visualizing the exogenously derived fibers within the lung specimen.

Fibers as small as about 2 microns can be detected and measured using the method of the present invention.

The present invention is an improvement over other procedures such as fluorescently labeled antibodies and color dyes such as haematoxilyn and eosin. For example, antibodies are exquisitely specific to particular epitopes expressed in or on cells and tissues and would not necessarily reveal morphologic features. Color dyes interfere with light transmission and, therefore, prevent viewing of subsurface tissue structure. The present invention requires far less time than serial sectioning and unlike ash analysis or serial sectioning, does not result in the destruction of the tissue.

The present invention uses non-specific fluorescent dyes such as Lucifer Yellow CH or Nile Red that bind to common cellular constituents and provide a suitable contrasting agent while under illumination by specific wavelengths of light.

DETAILED DESCRIPTION OF THE INVENTION

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Pathogenesis of disease caused by exogenously derived material within a tissue is dependent upon the type of material, solubility i.e., biopersistence and distribution within the tissue. For example, pathogenesis of fiber-induced lung disease is dependent upon the type of fiber, solubility i.e. biopersistence and distribution among the airway tree. However, fiber deposition following intratracheal instillation may not accurately represent fiber distribution in lungs exposed to a fiber-containing aerosol. Fibers with aspect ratios greater than 3:1 frequently deposit at airway bifurcations. Other factors such as the physical properties of the fibers themselves (wetability, solubility) also contribute to unpredictable fiber deposition. Fiber translocation or pulmonary clearance may be inhibited if large agglomerations of fiber are deposited at airway bifurcations as the result of the instillation process. The extent of fiber agglomeration in airways resulting from instillation is not known. However, the mere fact that agglomeration may occur could induce tremendous variability in fiber distribution and cloud the results of otherwise carefully controlled biopersistence studies as part of the regulatory certification process. The present invention provides a quick and thorough method to examine the distribution and quantity of foreign material in an intact biological specimen.

Figure 3A:
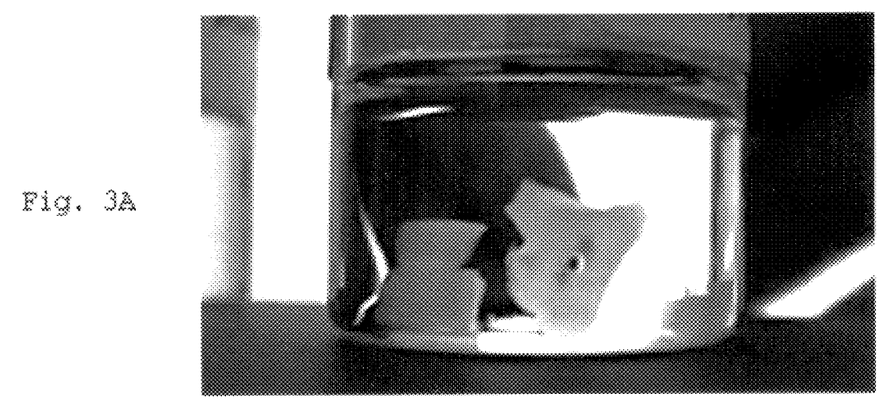
FIG. 3A is a photograph showing normal fixed rat tissue prepared in a conventional manner.
Figure 3B:
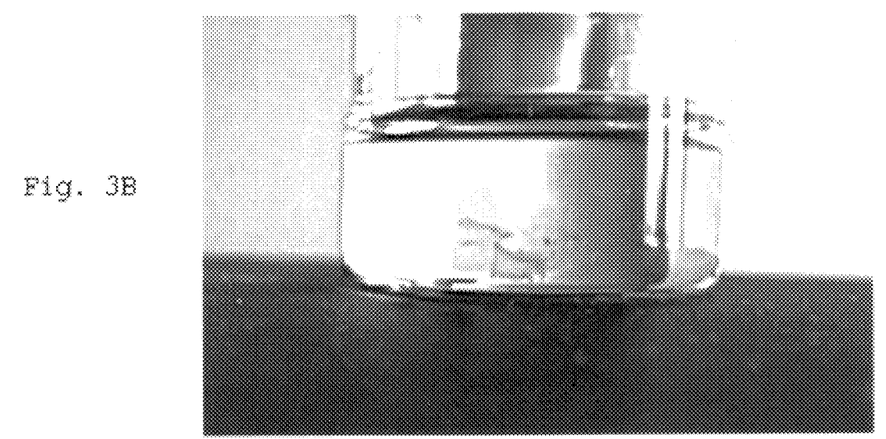
FIG. 3B is a photograph showing lung tissue that was subjected to the clearing procedure as described in the Exemplification.
Figure 3C:
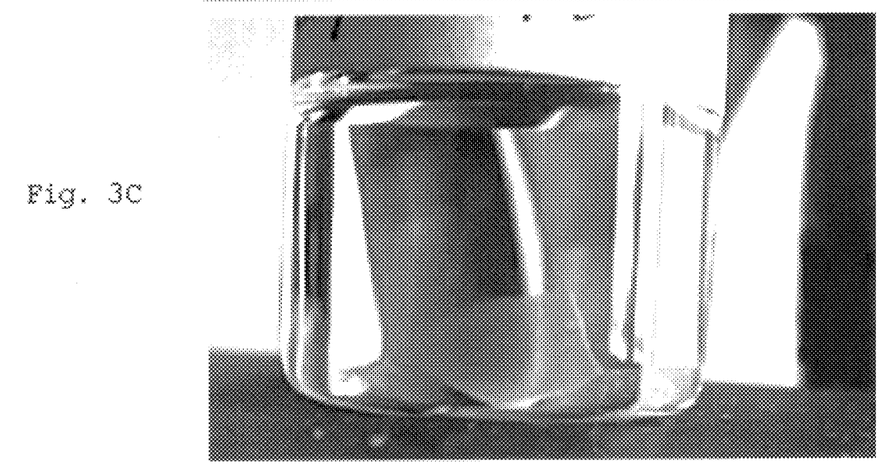
FIG. 3C is a photograph showing lung tissue cleared and fluorescently labeled by the method of the present invention, as described in the Exemplification.

The present invention relates to a method for clarifying and staining an intact biological specimen, wherein the biological specimen is rendered suitable for microscopic analysis of morphologic features at an unlimited depth within the specimen. FIG. 3A shows rat tissue prepared in a conventional manner. Note that light does not pass through the tissue. FIG. 3B and FIG. 3C show rat tissue subjected to the clearing and staining procedure of the present invention. Note that light passes through these specimens.

The method comprises the steps of: staining the specimen and equilibrating the stained specimen in a solution having the same refractive index as the specimen. The specimen can be depigmented prior to or after staining. Specific features such as specific epitopes or sequences of DNA or RNA can also be optionally labeled. Specific epitopes can be labeled with fluorescently-tagged antibodies using methods well known in the art. Specific DNA or RNA sequences can be labeled using labeled nucleic acid probes designed to hybridize the sequence of interest using methods well known in the art.

The biological specimen can be any tissue or sample of tissue of interest, such as tissues, organs, organ pieces, biopsies, sections or cells. The biological sample can be from invertebrates or vertebrates, including humans. The biological sample can be freshly isolated or preserved. In one embodiment, a mixture of the preserved sample is frozen. In another embodiment the preserved sample is dried. The specimen can be perfused prior or subsequent to isolation with a perfusate of choice.

The method is particularly useful to analyze the deposition, distribution, quantity, size and effect of exogenously derived material in or on the tissue of interest. The specimen can be exposed in vivo, to a substance of interest. The tissue of interest can be exposed to the material in vivo by a suitable route of exposure, such as inhalation, ingestion, injection, perfusion, instillation, application or absorption. Similarly, the tissue of interest can be exposed to the material in vitro by any suitable route of exposure, such as perfusion, injection, instillation, application or absorption. Methods of isolating specific tissues is well known in the art. The exogenous material can be, for example, a powder, particulate or fiber. The material can be man made or naturally occurring.

In one embodiment of the present invention, the specimen is immersed and fixed in an organic solvent comprising a dehydrating agent such as methanol, ethanol or octanol and a penetration enhancer such as dimethysulfoxide (DMSO), Tween-20™ Saponin or Triton X-100™. The specimen is incubated in the solve of about −70° C. to about −20 C. for several hours to overnight until the tissue is stabilized. The incubation time may be shortened by incubating at room temperature and/or gentle agitation of the solvent.

Upon stabilization, the specimen can be decolorized/depigmented/bleached by exposure to a solution comprising methanol, ethanol or octanol and DMSO and a depigmenting agent, such as potassium hydroxide, bleach, or hydrogen peroxide until desired effect of depigmentation is achieved. In one embodiment, a mixture of methanol and DMSO and 30% hydrogen peroxide is used. The specimen is then stained with a non-specific dye. In one embodiment, the dye is a fluorescent dye such as Lucifer Yellow CH, Nile Red, Rhodamine until such time (minutes to days) that dye penetration extends from surface features to the inner most central region of the specimen. In one embodiment, the staining is performed before the bleaching step. In a preferred embodiment, the staining follows the bleaching/depigmentation step. The specimen is then rendered optically clear, as viewed by white light, following immersion of the specimen in clearing solution, wherein the clearing solution such as paraffin oil, cedarwood oil, mixture of benzol alcohol/benzyl benzoate, silicon oil, or fluorocarbon having the same refractive index as the specimen. In one embodiment of the present invention, the specimen is rendered optically clear by equilibration in a 1:2 mixture of benzyl alcohol ($n_D$ 1.54035) and benzyl benzoate ($n_D$ 1.5681), also referred to herein as BABB. The specimen is incubated in the clearing solution until it is rendered transparent to visible light.

Optically cleared, stained specimens are mounted for microscopic examination. In one embodiment, the prepared specimen is placed in a glass bottomed microscope viewing chamber made of silicone rubber. The chamber is filled with maintaining fluid having the same refractive index as the specimen. In one embodiment, the mounting fluid and the clearing solution are the same. However, so long as there are no chemical incompatibilities nor any interference with the optical clarity of the mounted specimen, the clearing solution and mounting fluid need not be the same. The specimen is stabilized by silicon rubber pieces to prevent specimen movement within the chamber. A glass cover slip is applied to the viewing surface of the chamber, sealing the specimen within the chamber. The specimen is positioned in a manner immediately subjacent to the glass cover slip. The specimen is viewed using microscope objective (dry, water, oil immersion types) lenses attached to a confocal laser scanning microscope fitted with multiple fluorescent, bright-field, reflected light imaging device. A deconvolving microscope can also be used. A standard fluorescence microscope can also be used. The microscope should be equipped with a suitable light source, such as a xenon, mercury or tungsten lamp or an appropriate laser, such as an argon ion laser or argon krypton laser. To detect cell and tissue morphology, appropriate light, delivered at specific wavelengths to excite the fluorescent dye is used. For example, 488 nm wavelength can be used for Lucifer Yellow CH staining to obtain suitable contrast. In one embodiment, particulates such as fibers are viewed by trasmitted light. The method of the present invention allows the observation of man made or natural material within tissue in context with the labeled tissue structures. While lung tissue is specifically described in the Exemplification, it is understood that any tissue of interest could be used in the method of the present invention to achieve an optically clear specimen, suitable for microscopic analysis of morphologic features at an unlimited depth within the specimen.

Exemplification

Example I

Visualization of Glass Fiber in Rat Lung Tissues

Specimen Preparation

The specimen can be biological tissue (e.g., lung or other organs, glands, lymph nodes, muscle, bone, cartilage, or connective tissue). The specimen can be fresh, fixed, dried or frozen. The frozen biologic tissue can be held at liquid nitrogen temperature. If the sample is in liquid nitrogen or at −70° C., remove the sample from cryo storage and place on dry ice. If necessary, the sample can be modified to a smaller size, preferably following natural divisions in the tissue. For example, lung can be separated into right and left lungs or divided into individual lung lobes.

Specimen Fixation

Immerse tissue specimens (lung lobes) in fixative, such as methanol and DMSO at a ratio of 1:4 (Dent and Klymkowsky, *Development*, 105:61–74, 1989) at −70° C. at a displacement volume of at least 10 times that of the specimen. Incubate the specimen in fixative at low temperature (−70 to −20° C.) for several hours or overnight. Incubation time can be shortened by incubation at room temperature. During the incubation, replace the fixative with fresh fixative several times until tissue is stabilized. In the case of lung tissue, stabilization is indicated when tissue sinks. Gentle agitation on a low angle rotator or rocker facilitates the fixation process. To remove air bubbles and reduce fixation time, it may be necessary to apply a vacuum. Apply the vacuum in cycles of ever-increasing vacuum in a stepwise fashion. Stepwise vacuum increments of 5 cm $H_2O$/minute, cycled at 10 minute time intervals will remove air and minimize tissue displacement. A maximum of 25 cm $H_2O$ can be applied over time.

Specimen Depigmenting

Immerse the specimen in 100% methanol and DMSO fixative (4 parts methanol, 1 part DMSO) containing 30% hydrogen peroxide (2:1) (Klymkowsky and Hanken, *Methods in Cell Biol.* 36:420–441, (1991). The volume of the depigmenting solution should be 10 times that of the specimen. Replace the depigmenting fluid after 4 hours. Incubate the specimen in the depigmenting solution until desired effect is attained. The specimen should be uniformly opaque.

Non-Specific Staining

Immerse the depigmented specimen 100% methanol containing from about 0.001 to 0.1% Lucifer Yellow CH. This dye was selected because of its capacity to covalently bind to proteins and connective tissue in biological tissue. Other dyes such as Nile Red may also be used. Specimen staining for up to several days may be necessary, depending on the size of the specimen. Following non-specific fluorescent staining, unbound dye is removed by repeated immersion in 100% methanol for several hours.

Specimen Clearing

Place the specimen in a 1:2 mixture of benzyl alcohol ($n_D$ 1.54035) and benzyl benzoate ($n_D$ 1.5681)(BABB, after Murray and Kirschner, referenced in Klymkowsky and Hanken, 1991) until rendered transparent to visible light (several hours).

Mounting Specimens for Microscopic Viewing

Place the specimen in a glass-bottomed silicon rubber chamber filled with fresh BABB solution. Small pieces of silicone rubber or headless insect pins may be used to position the specimen in the desired orientation within the viewing chamber.

Microscopic Viewing

The confocal microscope records image data in a number of modes. Many combinations of the described imaging modes were possible, however, Mode 3 has provided the best results obtained.

Mode 1):

Single channel fluorescent imaging was used to record autofluorescent connective tissue surrounding airways in cleared lung specimens. This imaging mode was also optimized to collect images of airways and surrounding lung tissue from specimens labeled with Lucifer Yellow CH. Optical bench settings for the Sarastro 2000 confocal laser scanning microscope were; a) excitation, 488 nm (Lucifer Yellow CH), b) emission >510 long pass filter, c) laser power 20 mW, d) 3–10% transmission, e) photomultiplier tube (PMT) voltage set between 500–700 volts. Lucifer Yellow CH is optimally excited at the 457 nm line using an argon-ion laser, however, we have found that 488 nm light provides best contrast for morphologic determinations of tissue structure.

Mode 2)

Dual channel reflected and fluorescent imaging. Optical bench settings were the same as in single channel fluorescence, except, a 510 nm secondary beam splitter was placed in front of PMT-1, and directed short wavelength laser light from the fibers to PMT-2. Polarized light imaging capabilities of this microscope were enhanced, resulting in improved fiber imaging. Light entering the photomultiplier detector (PMT-2) was further filtered by placement of a narrow pass notch filter (488 nm) to eliminate unwanted fluorescent light (emitted from the specimen) from entering the detector. Fluorescent labeled cellular constituents and fibers (also particles) were imaged simultaneously with this arrangement.

Mode 3)

Dual channel transmitted light and fluorescent imaging. Optical bench settings were the same as in single channel fluorescence, except, an appropriate light filter (long pass 510 nm) was placed in front of the PMT to remove laser excitation light from the light emitted by the specimen. A light sensitive photodiode, termed a transmitted light detector, an optional imaging detector (manufactured by Molecular Dynamics, Sunnyvale, Calif.) attached to the microscope was positioned below the specimen on the microscope stage. Laser light (not emitted light from the specimen) passing through the specimen was collected by a condenser lens and focused on the transmitted light detector.

Image of fibers and other man-made materials not native to the biological tissue were imaged by the transmitted light detector due to a mismatch in refractive index of fibers and mount media, in this case BABB solution. Imaging Mode 3 revealed fluorescent cellular constituents and fibers (also particles) simultaneously.

To determine placement of fibers relative to the airway tree. Optical sections in the Z-axis were recorded by adjusting the stage height by stepper motors. Stacking section series in register and rendering the volume using 3-D imaging software (such as ImageSpace, Molecular Dynamics, Sunnyvale, Calif.) permitted three-dimensional reconstructions of both airways and fibers simultaneously. All imaging modes produced images as a matrix array (X,Y) of pixels, each with a unique intensity value from 0 to 254 gray scale units.

Position the mounted specimen on a confocal microscope fitted with a fluorescent lamp or a laser with a suitable wavelength. Bring desired structural features of the specimen into focus using fluorescent light of the appropriate wavelength. Record the fields of view using the laser scanning confocal mode of the instrument. If particular man-made or naturally occurring materials, such as fibers or particles are to be studied, examine the specimen under brightfield microscopy conditions to locate deposits of such material. Record a pair of images simultaneously, one image to reveal the tissue structure (made detectable by the non-specific Lucifer Yellow CH staining) and the other image to reveal the material in question (made visible due to the mismatch in refractive index with the BABB solution). Superimpose the digital image pairs to reveal the position of the deposited material relative to the lung structures under study.

Results

Figure 1:
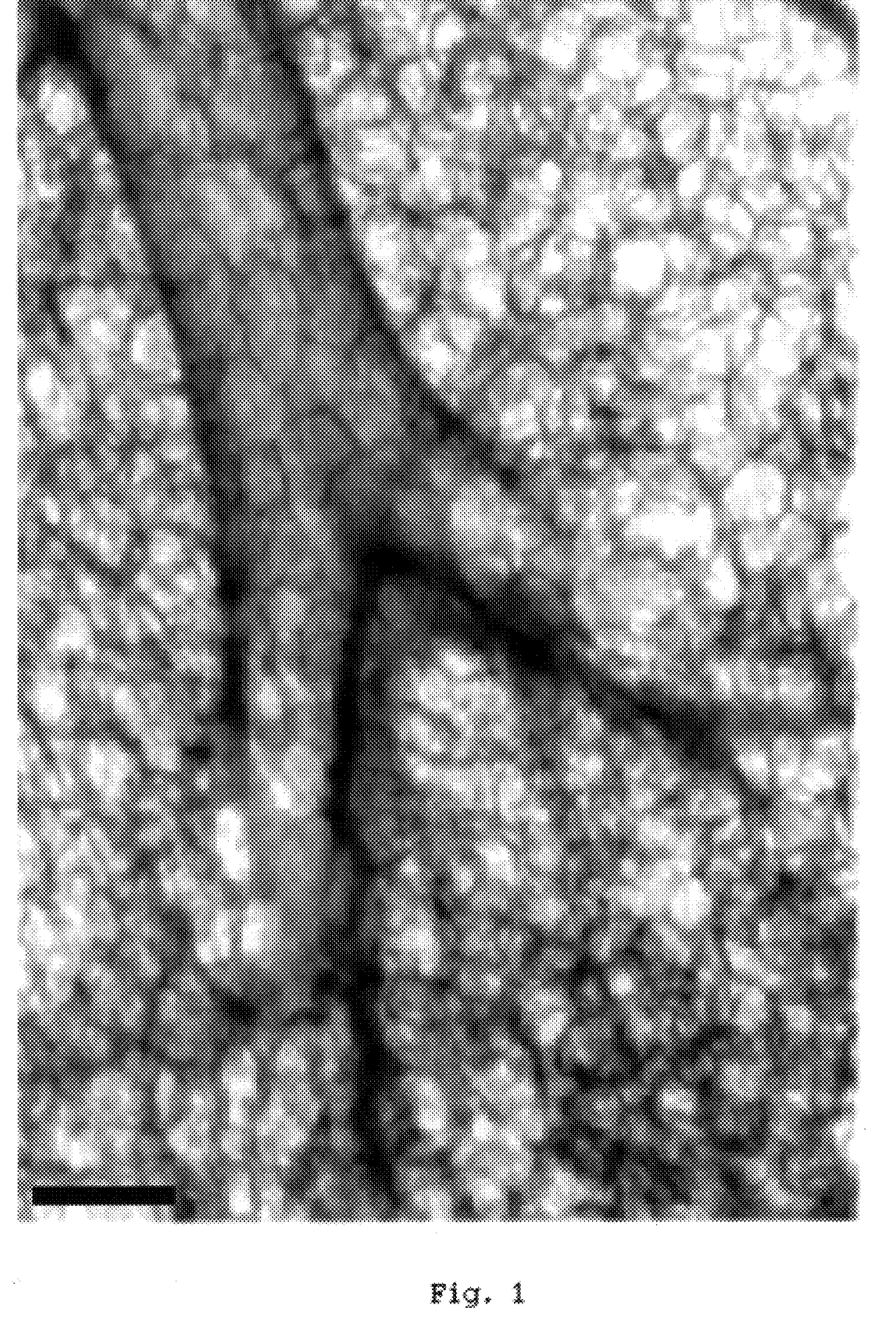
FIG. 1 shows an airway from a rat lung lobe subjected to the clearing protocol of the present invention. Bar is 100 microns. This particular airway was recorded from the central region of a piece of lung 3 millimeters thick.
Figure 2:
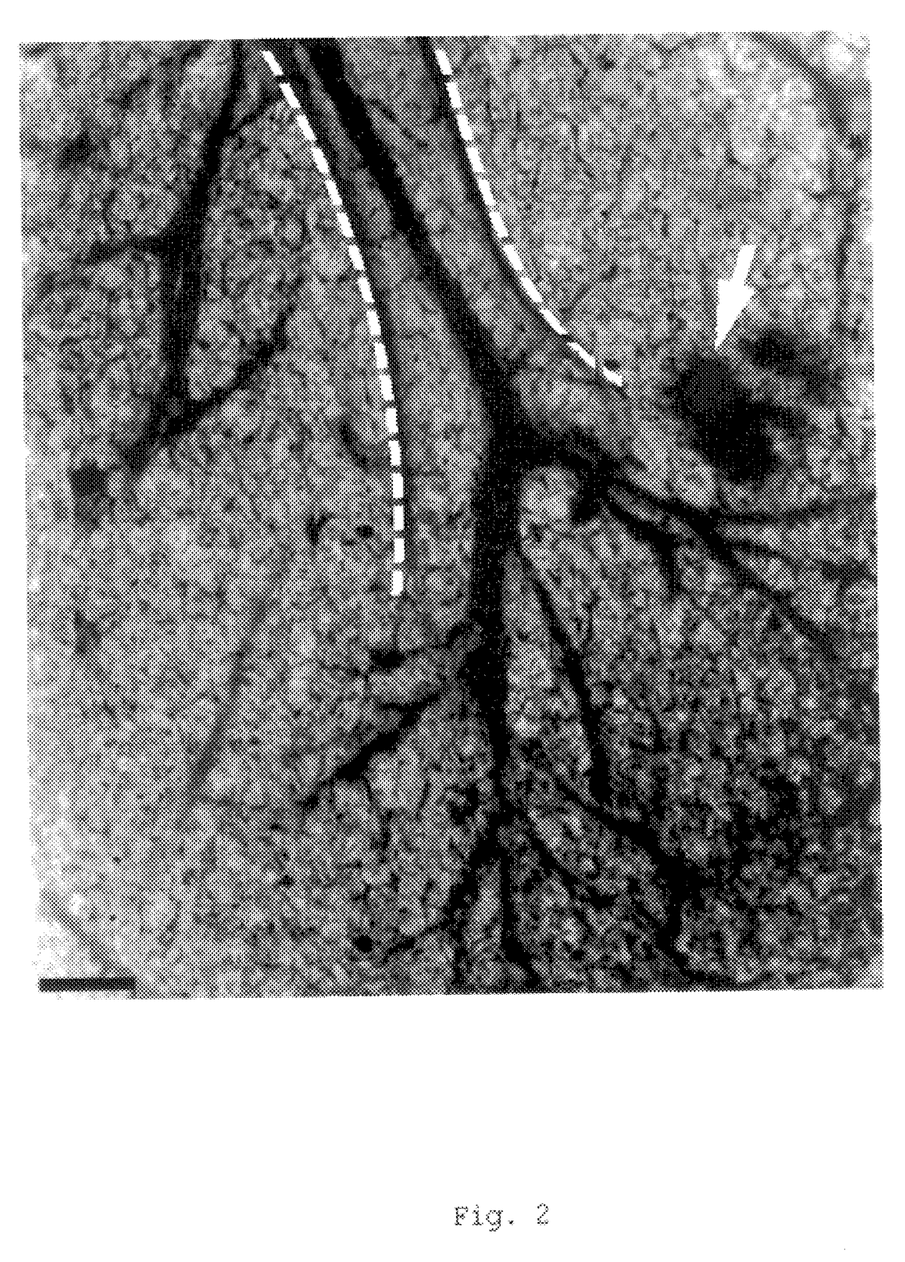
FIG. 2 shows an entire airway (lined with dash white lines) positioned below the blood vessel network (black) serving that airway. Of particular interest is an agglomeration of material (arrow) demonstrating our ability to detect and image foreign material delivered to airways via intratracheal instillation.
Figure 4:
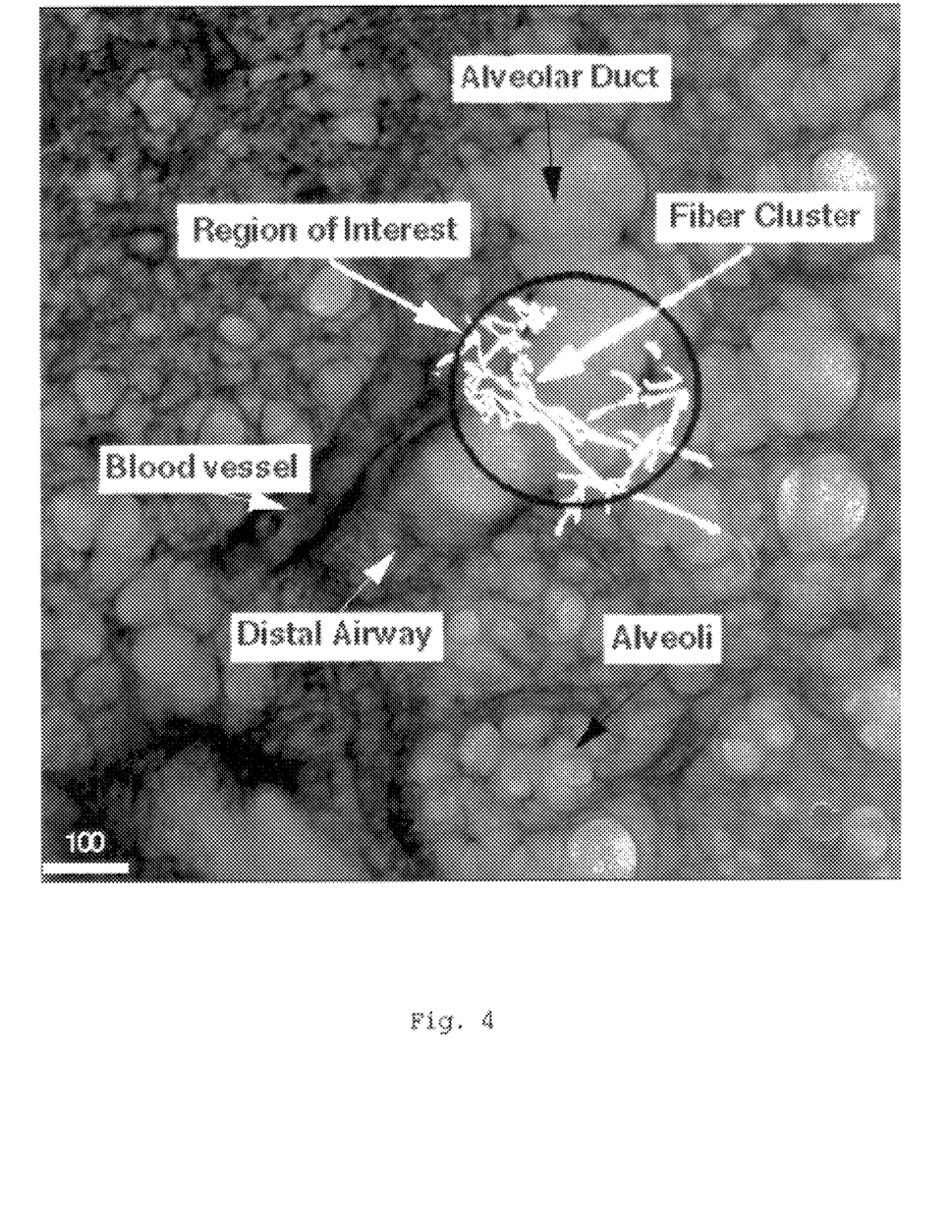
FIG. 4 is a photomicrograph showing fixed rat tissue superimposed with fibers visualized concurrently using transmitted light.

Deep frozen lung tissue (exposed in vivo to fibers by inhalation or intratracheal instillation) subjected to nonspecific fluorescent staining and tissue clearing procedure was used to detect, count, measure, and analyze manmade insulation fibers (from 0.2 to greater than 100 micrometers in length) deposited in lungs of test animals (rats) following intratracheal instillation. As shown in FIGS. 1, 2 and 4, the procedure revealed the presence and anatomic location of fibers within airways, and other pulmonary compartments.

Example II

Imaging of Fibers and Lung Tissue

Specimen Isolation and Shipment

Lungs from 14 animals were studied. Animals were exposed by intratracheal instillation of fibers (2 mg/ml) dispersed in a standard dose of physiological saline (150 microliters 1/100 g body weight) over a period of four consecutive days under controlled conditions in a chronic inhalation facility. One day after the last instillation, rats were killed and their lungs removed. Total lung weights were recorded, lungs divided into left and right, placed in plastic bags and frozen on dry ice for storage.

Lung lobes cryopreserved according to standard RCC frozen lung archive procedures (Research Consulting Co. Ltd., c/o Biological Research Laboratories Ltd., W ölferstrasse 4, CH-4414 Füllinsdorf, Switzerland) were shipped in cryostorage containers under liquid nitrogen to the imaging facility of Rogers Imaging Corporation for specimen preparation and microscopic analysis.

Specimen Processing

Deep frozen lung specimens stored in plastic bags held at −20° C. were placed in methanol and DMSO fixative (0° C.) in sealed glass vials for 12 hours. The specimens were then brought to room temperature. Fresh fixative was applied, and further processed.

Lung Depigmentation

Left lungs were depigmented according to the method of the present invention, as described under "Specimen Depigmenting" in Example I.

Lung Staining (Non-specific)

Left lungs were stained as described above in Example I.

Clearing Lung Procedure

Left lungs were fixed and cleared as described above. Lung clearing was determined empirically. Progress was monitored every 4 hours over a 24 hour period. Lung pieces were then placed in mount media (refractive index adjusted) as described above to optimize imaging.

Fibers in Dry Form

A small amount of fibers in dry form were subjected to the clearing lung procedure and were used for standardization purposes of the imaging equipment as described below.

Standardization of Image Recording Procedure

To standardize imaging parameters between imaging sessions, laser power was calibrated and uniform-field illumination was adjusted using a calibration slide. This procedure was followed each time the instrument was set up to record images for this project. Sensitivity of reflected light was checked using a calibration standard containing test fibers dispersed in the same embedding matrix as that used to embed the specimens included in the study. The sensitivity of the microscope was checked at the completion of every image recording session. Imaging parameters were optimized for fiber detection at all times. The sensitivity of the reflected light signal was adjusted so fibers were clearly identified. Because reflected light imaging is more sensitive to fiber orientation relative to the plane of focus, transmitted light was used to detect all possible fibers.

Detection and Quantification of Fibers, Fiber Length Measurement

To optimize detection of all possible fibers, dual channel transmitted light and fluorescent imaging was used. The microscope was configured for single channel fluorescence imaging. Optical bench settings were the same as in single channel fluorescence, except, an appropriate light filter (long pass 510 nm) was placed in front of the PMT to remove laser excitation light from the light emitted by the specimen. A light sensitive photodiode, termed a transmitted light detector, an optional imaging detector (manufactured by Molecular Dynamics, Sunnyvale, Calif.) attached to the microscope was positioned below the specimen on the microscope stage. Laser light (not emitted light from the specimen) passing through the specimen was collected by a condenser lens and focused on the transmitted light detector. Image of fibers and other man-made materials not native to the biological tissue were imaged due to a mismatch in refractive index of fibers and the mount media, in this case BABB solution. This imaging mode revealed fluorescent labeled cellular constituents and fibers (also particles) simultaneously. Images recorded provide a matrix (X, Y) array of pixels, each with a unique intensity value from 0 to 254 gray scale units. Optical sections in the Z-axis were recorded by adjusting the stage height by stepper motors. Individual fiber lengths were measured from projected images of all fiber profiles seen.

An alternate imaging mode using dual fluorescent and reflected light mode was used to detect fibers, but this mode has not been optimized at this time and therefore, only data from the dual channel transmitted light and fluorescent imaging is presented. Optical bench settings include a 510 nm secondary beam splitter placed in front of PMT-1, and directed polarized short wavelength light from the fibers to PMT-2. Polarized light imaging capabilities were enhanced to improve fiber imaging by placing a 488 nm notch filter in front of PMT-2. Lung tissue and fiber agglomerates were imaged simultaneously with this arrangement.

Fiber Distribution Index

To estimate fiber distribution in lung tissue, a "fiber Distribution Index" was calculated. The Fiber Distribution Index is based on those fields-of-view (131,072 microns$^2$) containing at least one 5–20 micron long fiber divided by all fields-of-view recorded. Fields of view were randomly collected at 400 times magnification.

Quantity and Size of Fiber Agglomerates

Since the method of the present invention enables entire lobes to be imaged, the number of fiber agglomerations can be determined using digital planimetry. Measurement of aggregate size was determined by measuring the distance (in micrometers) through a fiber clump. Useful morphometric data such as quantification of structures, point to point distances, number of occurrences per field, and diameter measurements of fiber aggregates were obtained directly from images.

Lung Area Occupied by Fiber Agglomerations

Lung tissue was systematically examined to locate fiber agglomerations in airways. Fields-of-view were recorded and the area of each micrograph noted. Fiber clump areas were determined.

Fiber Agglomeration Index.

A Fiber Agglomeration Index was calculated by dividing the number of agglomerations by the number of fields-of-view containing at least 4 fibers (5–20 microns). Use of fields-of-view containing at least 4 fibers was chosen based on an average of 4 fibers per field-of-view calculated from an inhalation exposure determination at a similar time point.

Results

Length Distribution of Fibers

Figure 5A:
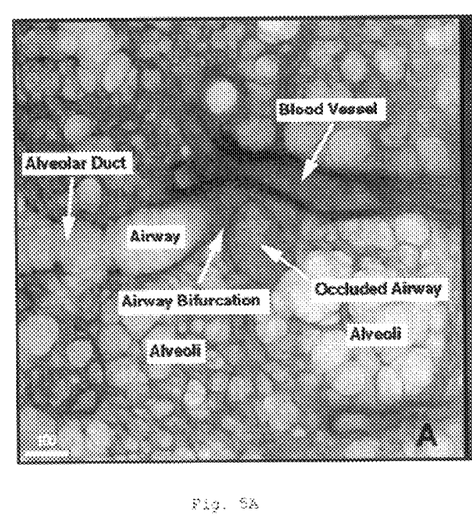
FIG. 5A is a photomicrograph of lung features as revealed by the method of the present invention.
Figure 5B:
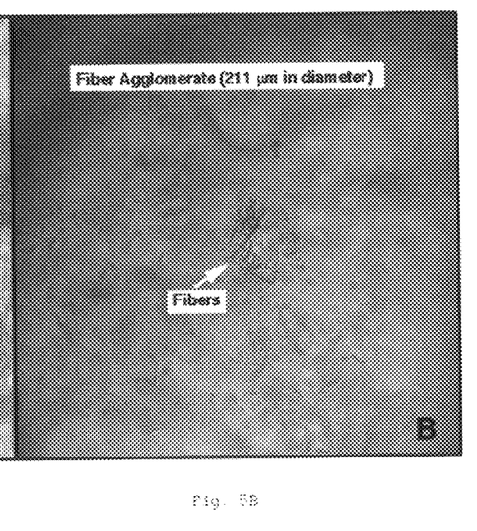
FIG. 5B is a photomicrograph of the same field as 5A, taken simultaneously with transmitted light, revealing a fiber agglomerate.
Figure 6:
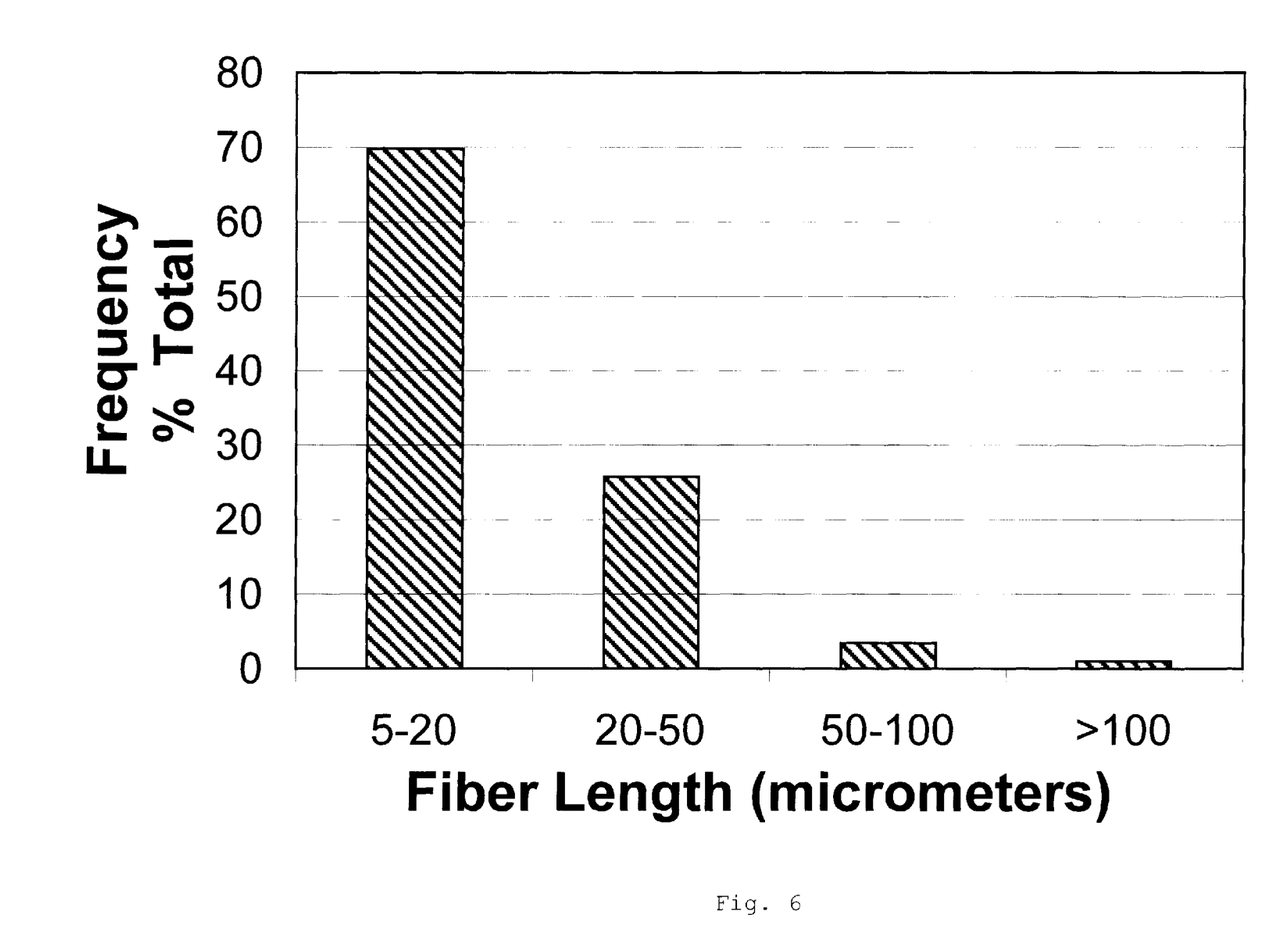
FIG. 6 is a bar graph of in situ length distribution of glass fibers.

A total of 672 fields of view were examined from the fourteen animals received. The in situ length distribution of fibers in airways are presented in FIGS. 5A and 5B and 6. A total of 10,743 fibers were counted.

Fiber Distribution Index

A Fiber Distribution Index of 0.72 was determined, less than that observed in animals receiving fiber exposure by inhalation.

Fiber Agglomerations

Figure 7:
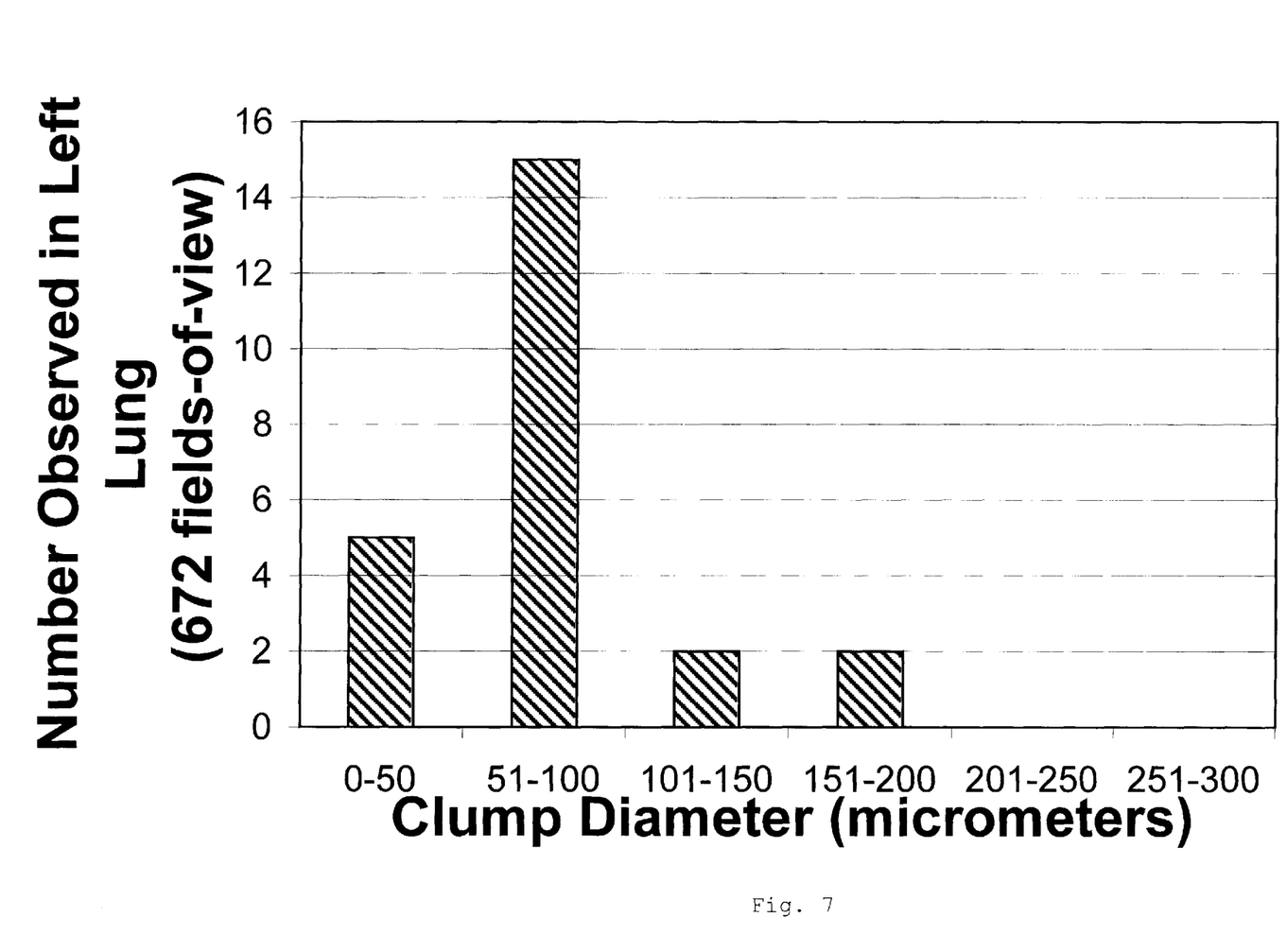
FIG. 7 is a bar graph of in situ fiber clump diameter.

Fiber agglomerations (or clumps) were observed in 3.6% of the fields-of-view. The average fiber agglomeration diameter was 99 microns (FIG. 7). Fiber agglomerations occupied 0.23% of the lung area examined. An Agglomeration Index of 0.07 was determined.

Qualitative Evaluation

Lung tissue appeared normal. Inflammatory cells were seen in the occluded (rare) airways.

Fibers were less evenly distributed than what is seen in inhalation exposure animals. No fibers could be detected in several large regions of the lung, typical of instillation exposure. In regions where fibers were found, many airways contained fibers dispersed on airway walls. Fibers appeared to be "bunched up" at airway bifurcations and rarely occluded the airway lumen. Fibers were also observed in small airways (less than 100 microns) down to the alveolar duct level. Fibers were commonly seen in alveoli.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of visualizing foreign material present in lung tissue and of visualizing pathology of the lung tissue associated with the foreign material, comprising the steps of:

a) contacting the lung tissue with a fluorescent dye, wherein the dye stains the lung tissue non-specifically;

b) equilibrating the non-specifically stained lung tissue in a clearing solution, wherein the refractive index of the clearing solution approximates that of the lung tissue; and c) visualizing the foreign material in the lung tissue and morphology of at least a portion of the lung tissue contacting the foreign material whereby pathology of the lung tissue associated with the foreign material is revealed.

2. The method of claim 1, wherein the fluorescent dye is selected from the group consisting of: Lucifer Yellow CH, Nile Red and rhodamine.

3. The method of claim 1, wherein the foreign material includes at least one fiber.

4. The method of claim 3, further including the step of administering the fibers to the lung tissue prior to contacting the lung tissue with the fluorescent dye.

5. The method of claim 4, wherein the fibers are administered by injection, inhalation or perfusion.

6. The method of claim 3, wherein the fiber is at least about 0.2 microns in length.

7. A method of visualizing foreign material present in lung tissue and of visualizing the morphology of a portion of the lung tissue contacting the foreign material, comprising the steps of:

a) contacting the lung tissue with Lucifer Yellow CH, wherein the Lucifer Yellow CH stains the lung tissue non-specifically;

b) equilibrating the non-specifically stained lung tissue in a clearing solution, wherein the refractive index of the clearing solution approximates that of the lung tissue; and c) visualizing the foreign material in the lung tissue and the morphology of at least a portion of the lung tissue contacting the foreign material.

8. The method of claim 7, wherein the foreign material includes at least one fiber.

9. The method of claim 8, further including the step of administering the fibers to the lung tissue prior to contacting the lung tissue with Lucifer Yellow CH.

10. The method of claim 9, wherein the fibers are administered by injection, inhalation or perfusion.

11. The method of claim 8, wherein the fiber is at least about 0.2 microns in length.

* * * * *